United States Patent [19]

Perry

[11] Patent Number: 5,215,460

[45] Date of Patent: Jun. 1, 1993

[54] METHOD FOR PARALLELING IMPLANT RESTORATIVE COMPONENTS

[76] Inventor: William L. Perry, 1517 Live Oak, Irving, Tex. 75061

[21] Appl. No.: 795,867

[22] Filed: Nov. 20, 1991

[51] Int. Cl.⁵ .............................................. A61C 3/00
[52] U.S. Cl. ..................................... 433/75; 433/173
[58] Field of Search ..................... 433/75, 76, 72, 74, 433/173, 215

[56] References Cited

U.S. PATENT DOCUMENTS

| | | | |
|---|---|---|---|
| 1,189,753 | 7/1916 | Thue | 433/76 |
| 4,645,453 | 2/1987 | Niznick | 433/173 |
| 4,832,601 | 5/1989 | Linden | 433/173 |
| 4,906,191 | 3/1990 | Soderberg | 433/173 |
| 5,015,186 | 5/1991 | Detsch | 433/74 |

*Primary Examiner*—John J. Wilson
*Attorney, Agent, or Firm*—David H. Judson

[57] ABSTRACT

A method is described for fabricating a dental prosthodontic restoration to be fitted on at least first and second implant fixtures, each of the implant fixtures supporting an abutment. The method begins by fitting a first abutment screw assembly to said first implant fixture, the first abutment screw assembly including a screw portion, and an attachment secured to the screw portion. The first abutment screw assembly is then tightened to retain the assembly in the first implant fixture. Then, the method continues by fitting a screw portion of a second abutment screw assembly to said second implant fixture and tightening the screw portion to the second implant fixture. Using an intra-oral jig mechanism, the attachment of the second abutment screw assembly is then located in a predetermined position relative to the screw portion thereof such that the attachments of the first and second abutment screw assemblies have a parallel orientation. The method can alternatively be practiced using two-piece assemblies.

14 Claims, 5 Drawing Sheets

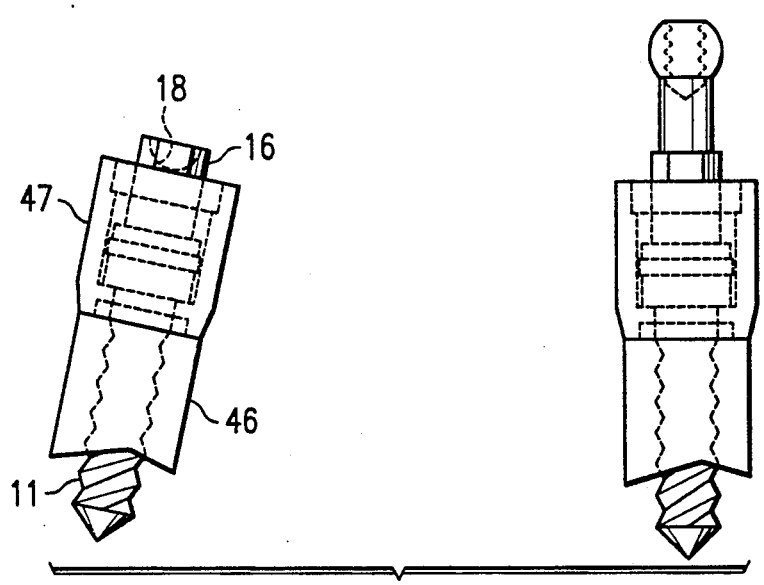
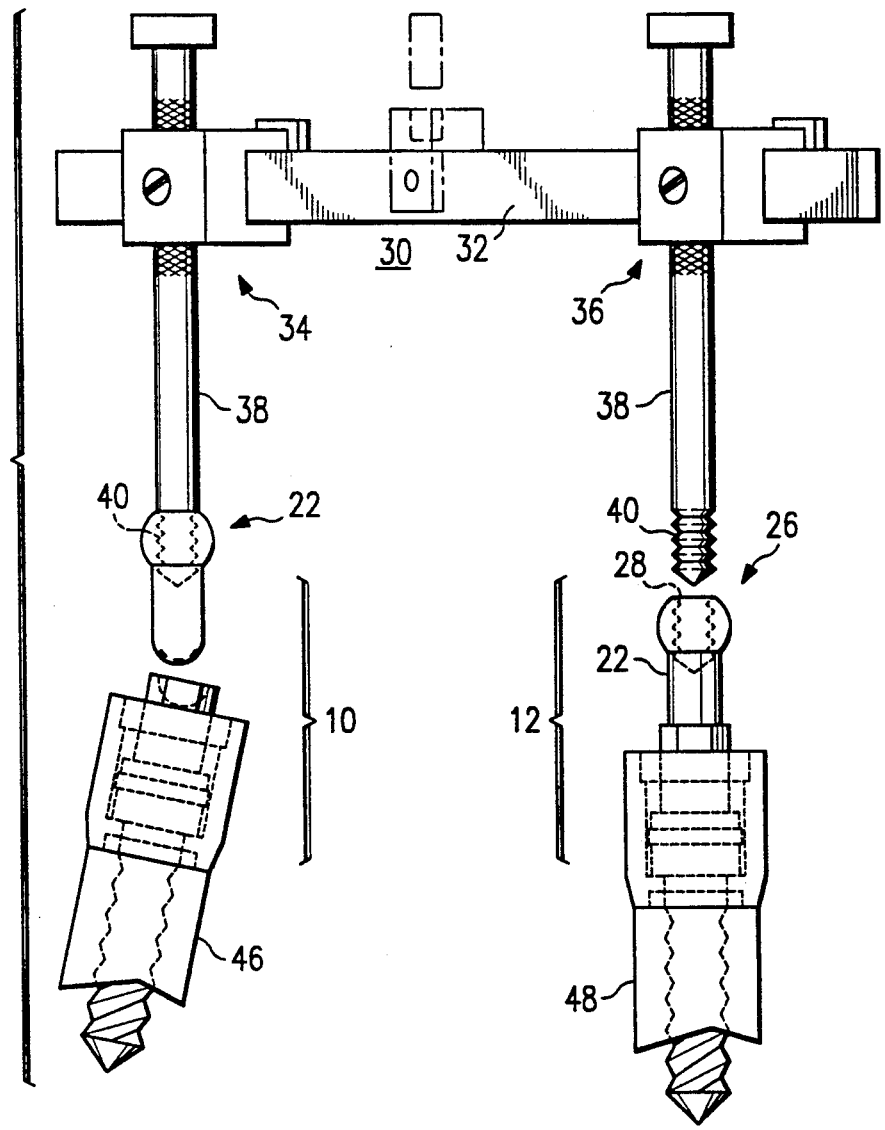
FIG. 5
FIG. 6 ical field

The present invention relates generally to restorative dentistry and more particularly to a method and system for paralleling implant restorative component fixtures used to support a fixed, fixed-removable or removable prosthesis.

BACKGROUND OF THE INVENTION

Traditional overdenture attachments, "cement-to" abutments and screw retention abutments are useful in implant restorative dentistry. Most free-standing overdenture attachment, "cement-to" abutments and screw retention abutments are designed to screw into an implant fixture. In multi-tooth restorations, a plurality of implant fixtures are used to support a prosthesis that is fabricated using an impression. While such systems have proven advantageous, they have not been widely implemented in part due to problems associated with the nonparallel placement of implant fixtures. If the fixtures are significantly nonparallel, undercuts are present which prevent "draw" of the prosthesis that is to be placed on the attachment/abutments. Also, many attachment systems are designed with the assumption that the attachments will be parallel. Such systems either will not function or function ineffectively otherwise.

There is therefore a need to provide techniques that overcome the problems associated with and/or compensate for nonparallel placement of implant fixtures.

BRIEF SUMMARY OF THE INVENTION

It is an object of the present invention to eliminate the limitations of prior art dental restoration techniques wherein an overdenture or prosthesis is supported on a plurality of implant fixtures.

It is still another object of the invention to provide a method and apparatus for effectively "paralleling" implant fixtures by direct or indirect methods to facilitate proper support of the overdenture or other type of prosthesis.

These and other objects of the present invention are provided in a method and system for paralleling implant restorative components. In one embodiment, a method is described for fabricating a dental prosthodontic restoration to be fitted on at least first and second implant fixtures, each of the implant fixtures supporting an abutment. The method begins by fitting a first abutment screw assembly to said first implant fixture, the first abutment screw assembly including a screw portion, and an attachment secured to (or otherwise integrally-formed with) the screw portion. The first abutment screw assembly is then tightened to retain the assembly in the first implant fixture. Then, the method continues by fitting a screw portion of a second abutment screw assembly to said second implant fixture and tightening the screw portion to the second implant fixture.

Using a jig mechanism (either intra-orally or on a working model), the attachment of the second abutment screw assembly is then located in a predetermined position relative to the screw portion thereof such that the attachments of the first and second abutment screw assemblies have a parallel orientation.

After paralleling the attachments using the jig, the attachment of the second abutment screw is secured in the predetermined position using a resin material, preferably Duralay ™ resin. The screw portion of the second abutment screw assembly with the attachment secured thereto is then removed from the second implant fixture. Thereafter, the composite is burned away by an investment procedure while the attachment is maintained against movement relative to the screw portion. Finally, the attachment is soldered to the screw portion and the resulting second abutment screw assembly is fitted to the second implant fixture. The attachments of the first and second abutment screw assemblies are then paralleled. An overdenture or prosthesis is then formed on the paralleled attachments of the first and second abutment screw assemblies.

Alternatively, the method can be practiced indirectly (i.e., outside the oral cavity) by using an impression (with proper component indexing) along with the jig, a working model and a surveyor.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 5 is an elevational view of a step of the method wherein a screw portion of a "two-piece" abutment screw assembly is secured to the other of the fixtures;

FIG. 6 is an elevational view of a step of the method wherein the intra-oral attachment jig is set to be attached to the screw assemblies with the attachment of the two-piece assembly already in place;

Similar reference characters refer to similar parts throughout the several views of the drawings.

DETAILED DESCRIPTION

Figure 1:
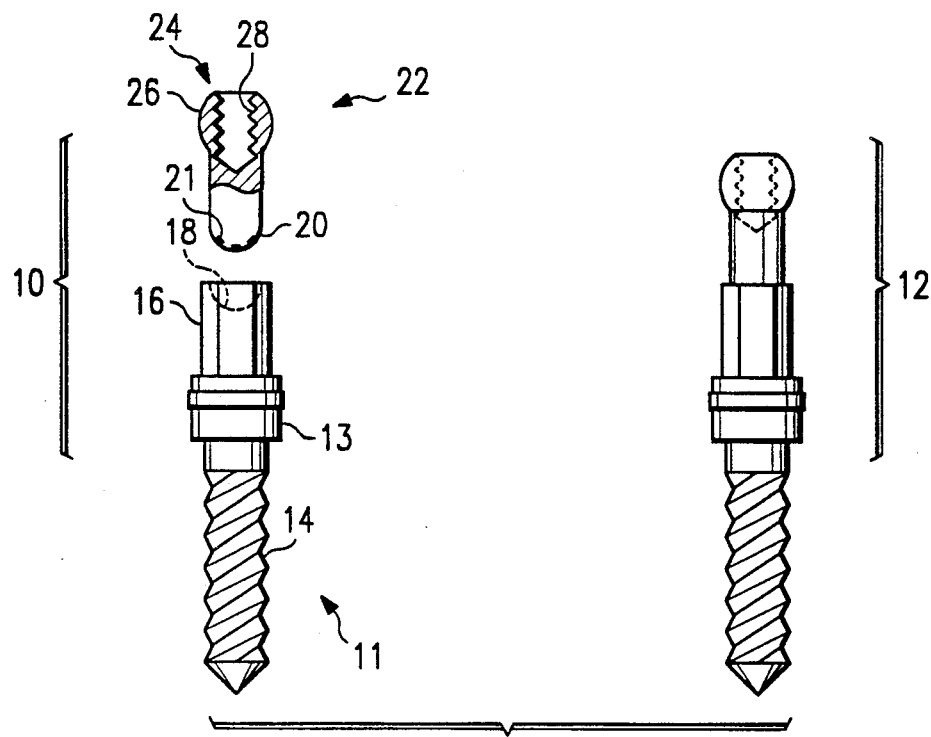
FIG. 1 is an elevational view of the two types of abutment screw assemblies used in accordance with the teachings of the present invention.

The teachings of the present invention are generally applicable to multi-tooth, partially-edentulous, fully-edentulous or fixed-removable restorations. As is well-known in the prior art, such restorations typically include several dental implant fixtures, with each fixture being implanted in a cylindrical bore made in the alveolar ridge crest of a patient's jawbone after the gum tissue has been displaced. A coronal end of the fixture has at its gingival aspect a transverse surface that is substantially flush with the alveolar ridge crest after the fixture is implanted. The implant fixture has an internally-threaded socket or indentation opening to its gingival surface, upon which a fitting is fixed. After the implant fixture has osseointegrated with the jawbone of the patient, an abutment is attached to the fixture through an opening in the overlying gum tissue. A bore passes completely through the abutment. When the abutment is fitted to the bone surface, an abutment screw is screwed into the internally-threaded socket of the implant fixture.

When two or more of the implant fixtures osseointegrate in the patient's bone (either maxilla or mandible), the fixtures may be oriented in a nonparallel fashion. Such orientation causes significant problems when the prosthesis is supported thereon. To overcome these problems, and with reference now to FIG. 1, the method and system of the invention utilizes a "two-piece" abutment screw assembly 10 and a "one-piece" abutment screw assembly 12 to facilitate compensation for nonparallel placement of implant fixtures. The two-piece abutment screw assembly 10 includes a screw portion 11 and an attachment 22. The attachment is a "ball" type for illustrative purposes only. According to the invention, any type of attachment, including traditional overdenture, "cement-to" or screw-retention types, may be used. The screw portion comprises a central body portion 13, and an externally threaded shaft 14 intended to mate with the internally-threaded socket (not shown) in an implant fixture. A male hexagonal fitting 16 is attached to or integrally-formed with the body portion 13 at its superior end. Fitting 16 is especially adapted to receive a locking sleeve for preventing rotation of the screw assembly. Such construction is described in applicant's copending application Ser. No. 07/715,507, filed Jun. 14, 1991, titled "Non-Rotational Dental Restoration", now U.S. Pat. No. 5,108,288 which application is incorporated herein by reference. Fitting 16 includes a semi-circular indentation 18. Alternatively, the outer periphery of the fitting 16 can have any appropriate shape.

The indentation 18 is adapted to receive a rounded inferior end 20 of the attachment 22 so that the attachment 22 is pivotally adjustable relative to the indentation. Such pivotal adjustment of the attachment 22 facilitates the method of the invention by enabling the placement of a superior end 24 of the adjustment 22 to be horizontally and vertically adjusted. The rounded inferior end 20 of the attachment 22 may include one or more tapered cutouts 21 in which solder can be retained. The intimate surface contact between the indentation 18 and the end 20 along with the mechanical retention of the solder enables the attachment joint to handle optimal shear, compression and tensile loading.

The superior end 24 of the attachment 22 includes a ball fitting 26, which as described above is merely illustrative, having an internally-threaded socket 28 for the purposes to be described. The one-piece abutment screw assembly 12 is essentially similar in construction except that the attachment 22 is fixed (through soldering or other suitable means such as milling, forging or machining) to the fitting 16 of the screw portion 11. The height of the fitting is variable depending on the size of the abutment. Also, the specific structure of the central body portion 13 will depend on the type and make of the abutment in which the screw assembly is received. Thus the teachings of the present invention are applicable to any type of attachment, "cement-to" abutment or screw retaining abutment including, without limitation, a ball attachment as shown, ERA type attachment, OSO type attachment, Zest type attachment, o-ring type attachment, tapered abutment type head, etc.

Figure 2:
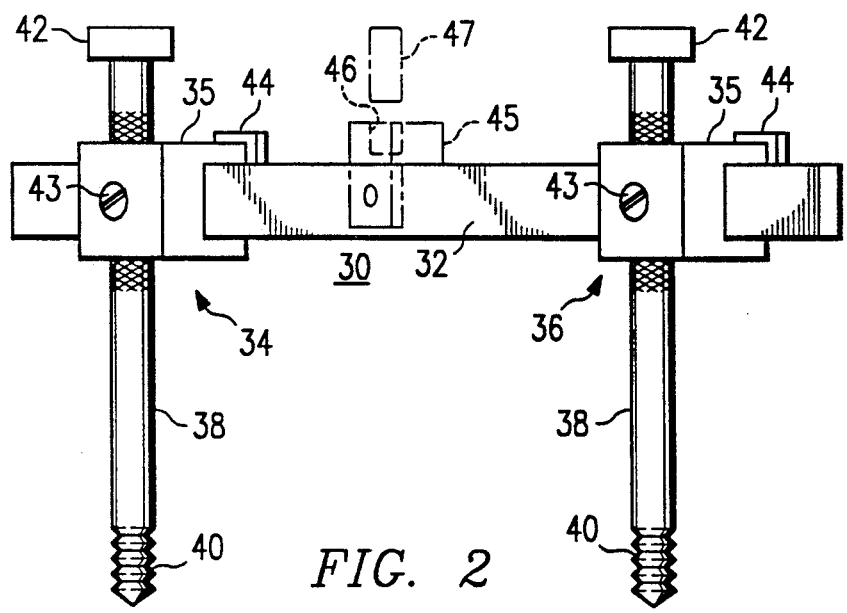
FIG. 2 is an elevational view of an intra-oral attachment jig for use in accordance with the present invention.

Referring now to FIG. 2, an elevational view is shown of an attachment jig 30 for use intra-orally or extra-orally in accordance with the present invention. Jig 30 comprises a cross-member 32 having first and second lateral adjustment assemblies 34 and 36. Each of the adjustment assemblies includes a positioning sleeve 35, and a post 38. Post 38 is perpendicular to cross-member 32 and has a threaded shaft 40 at one end and a finger grip 42 at the other. The finger grip is adapted to work with a torque driver system as more particularly described in applicant's copending application Ser. No. 07/720,948, filed Jun. 25, 1991, titled "System For Driving And Tightening Components In A Prosthondontic Restoration," which application is incorporated herein by reference. The post 38 is adapted for vertical (i.e., up and down) movement within the adjustment assembly and the positioning sleeve 35 facilitates lateral, i.e., horizontal, movement of each adjustment assembly on the cross-member 32. A set screw 43 (or other type of securing mechanism) is used to retain the post at a predetermined vertical position. A friction lock 44 is used to retain the positioning sleeve at a predetermined lateral position on the cross-member 32 as will be described.

Figure 3:
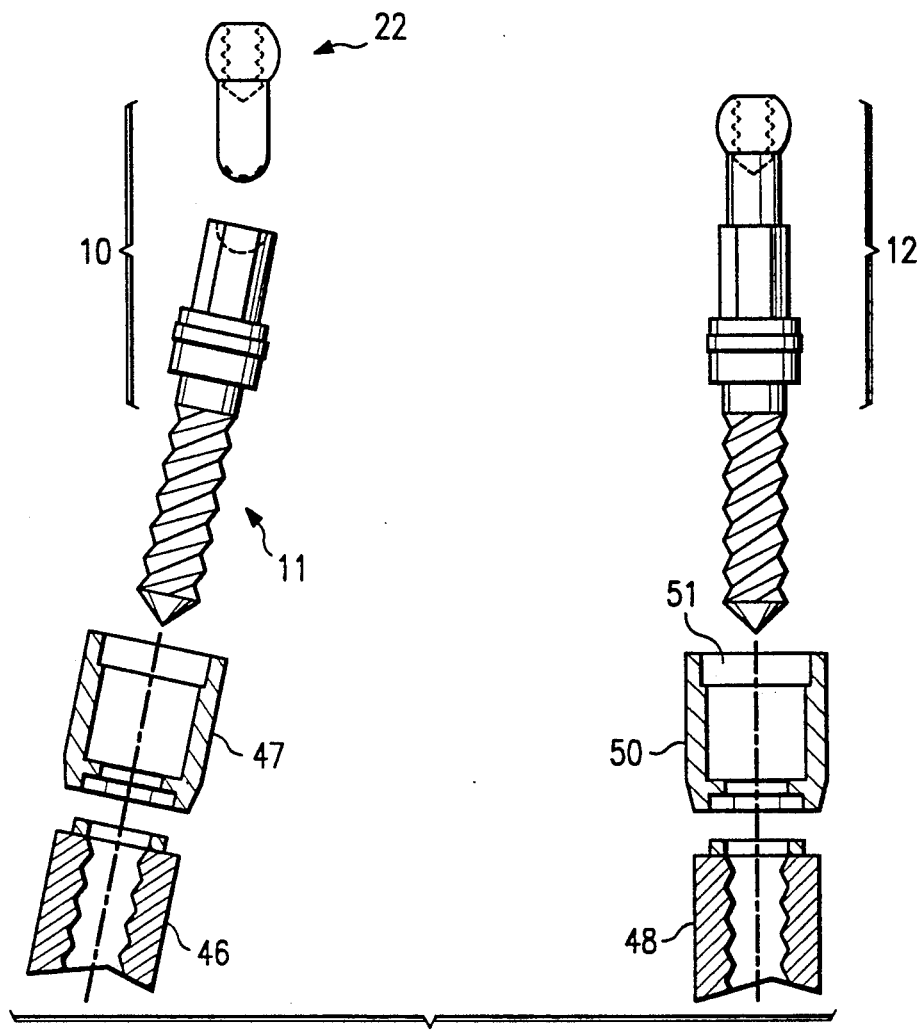
FIG. 3 is a elevational view, partially exploded, showing a pair of implant fixtures whose orientation is paralleled according to the method of the invention.

With the above background, the method of the present invention can now be described in detail. FIG. 3 is a elevational view, partially exploded, showing a pair of implant fixtures 46 and 48 whose orientation is desired to be paralleled according to the method of the invention. It should be appreciated that the techniques of the invention do not physically move the implant fixtures 46 and 48 relative to each other to provide such parallel orientation, as such fixtures are osseointegrated into the jawbone. Rather, the technique compensates for any nonparallel or other misalignment between such fixtures.

Figure 4:
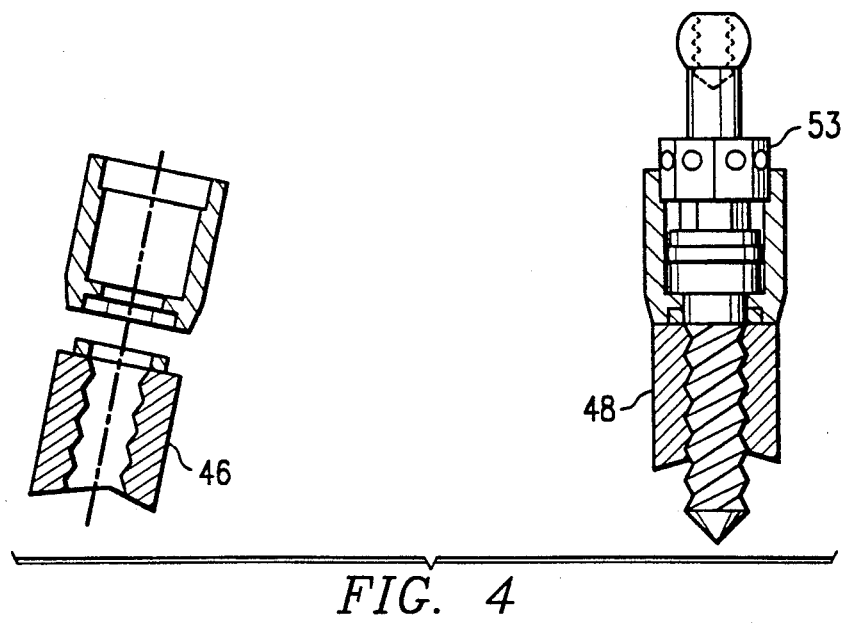
FIG. 4 is an elevational view of the first step of the method wherein a "one-piece" abutment screw assembly is secured within one of the fixtures.

For purposes of example only, it is assumed that implant fixture 48 is the correct position for restoration and that fixture 46 is an a nonparallel alignment with respect thereto. Thus, in the preferred embodiment, a one-piece assembly 12 is used for the fixture 48 while a two-piece assembly 10 is used for the fixture 46 whose orientation is to be compensated. To begin the method, an appropriate standard abutment 50 of the engaging or non-engaging type is selected depending on the height of the transmucosal tissue. A suitable abutment 47 is also selected for the fixture 46. Referring now to FIG. 4, after the abutment 50 is placed on the implant fixture 48, the one-piece abutment screw assembly 12 (of appropriate size depending on the abutment 50 selected) is then screwed into the implant fixture 48. The abutment screw assembly is tightened to a predetermined torque using a suitable driver system, for example, as described in applicant's copending application Ser. No.

07/720,948, filed Jun. 25, 1991, now U.S. Pat. No. 5,158,458. Moreover, and as described in the above-identified copending application Ser. No. 07/715,507, filed Jun. 14, 1991, preferably the space located between the fitting 16 and the superior socket 51 of the abutment 50 is filled with a locking sleeve 53 or a suitable composite material to prevent rotation of the abutment screw assembly 12. The abutment assembly is then complete.

Referring now to FIG. 5, the other fixture 46 receives the abutment 47. Thereafter, the screw portion 11 of the two-piece abutment screw assembly 10 is screwed into the fixture 46 and torque driver. Referring now simultaneously to FIGS. 2 and 6, the method continues with the user attaching the attachment portion 22 of two-piece abutment screw assembly 10 to the threaded shaft 40 of the post 38 in the first adjustment assembly 34 of the intra-oral jig 30. The threaded shaft 40 of the post 38 in the second adjustment assembly 36 is screwed into the internally-threaded socket 28 of the ball fitting 26, which is illustrative only, of the one-piece assembly 12 located on fixture 48.

Figure 7:
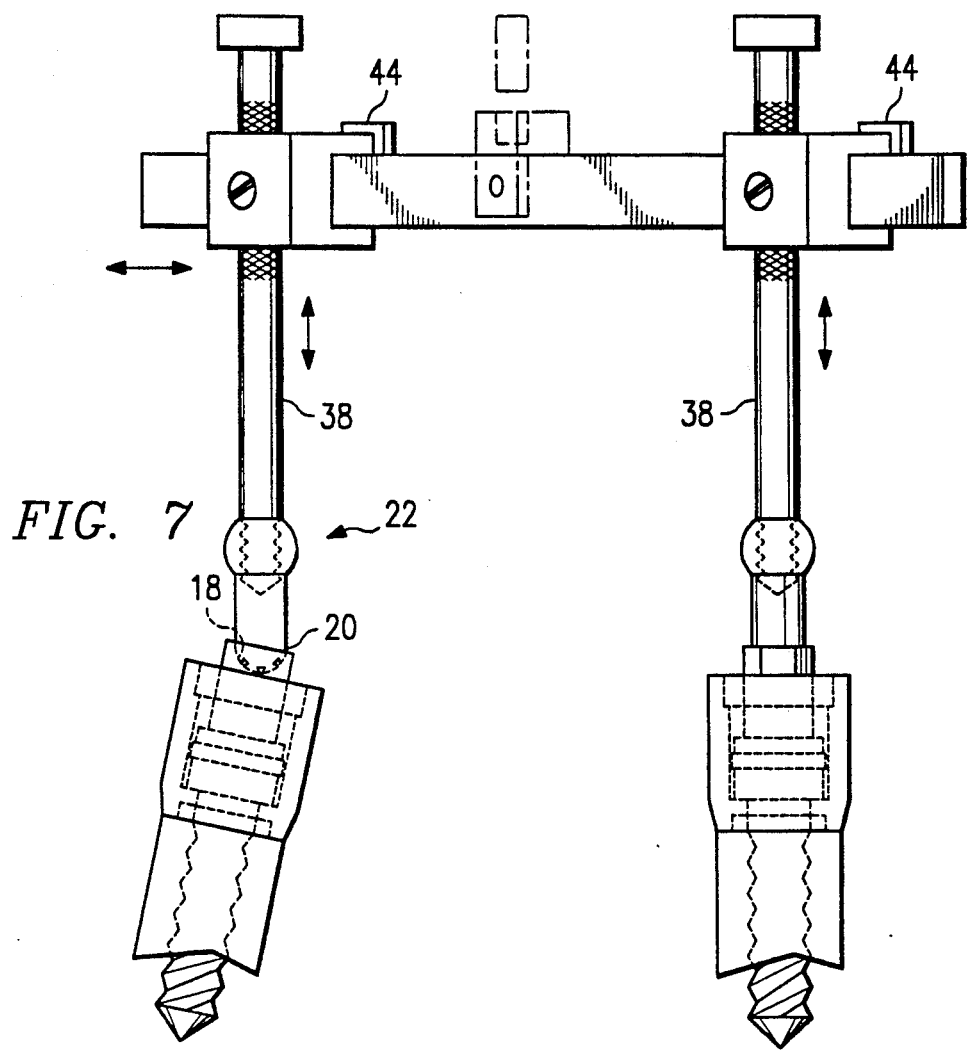
FIG. 7 is an elevational view of a step of the method wherein the intra-oral attachment jig is attached to the one-piece screw assembly.

Referring now to FIG. 7, the attachment 22 of the two-piece abutment screw assembly 10 is then positioned onto the screw portion 11 by adjusting the relative vertical and horizontal position of the post 38 in the first adjusting assembly 34. This operation enables the orientation of the attachments in each assembly 10 and 12 to be made parallel according to the teachings of this invention. Once the proper position of the post 38 is found to establish such parallelism, the friction locks 44 and set screws 43 of the jig 30 are set to prevent movement of the posts 38 from their positions. The inferior end 20 of the attachment 22 is then located in the indentation 18 of the fitting 16. The attachment 22 and the screw portion 11 of the two-piece assembly 10 are then bonded together with a hardenable resin material such as Duralay ™ and allowed to cure. Duralay ™ resin is available from Reliance Dental Manufacturing Company. Another useful composition is GC pattern resin made by GC Dental Industrial Corporation.

Figure 8:
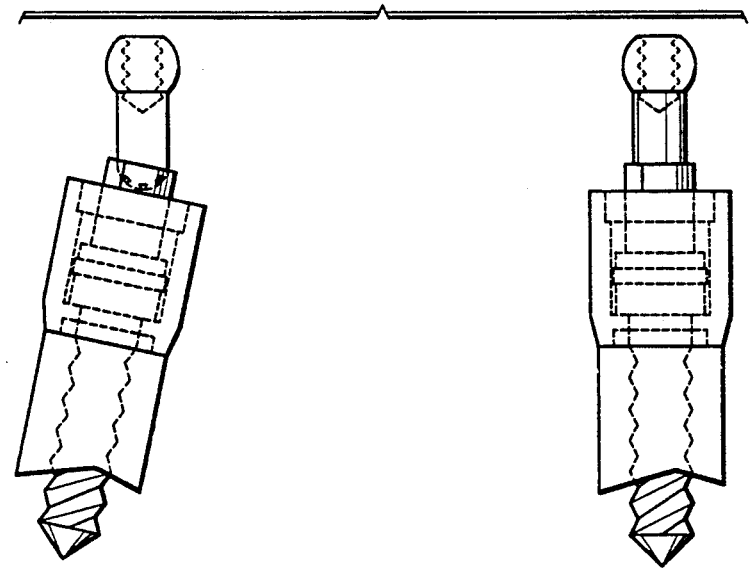
FIG. 8 is an elevational view of a step of the method after the intra-oral attachment jig has been removed from the implant fixtures.
Figure 9:
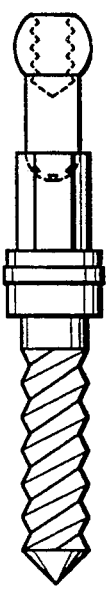
FIG. 9 is an elevational view of the two-piece abutment screw assembly after it has been removed from the implant.
Figure 10:
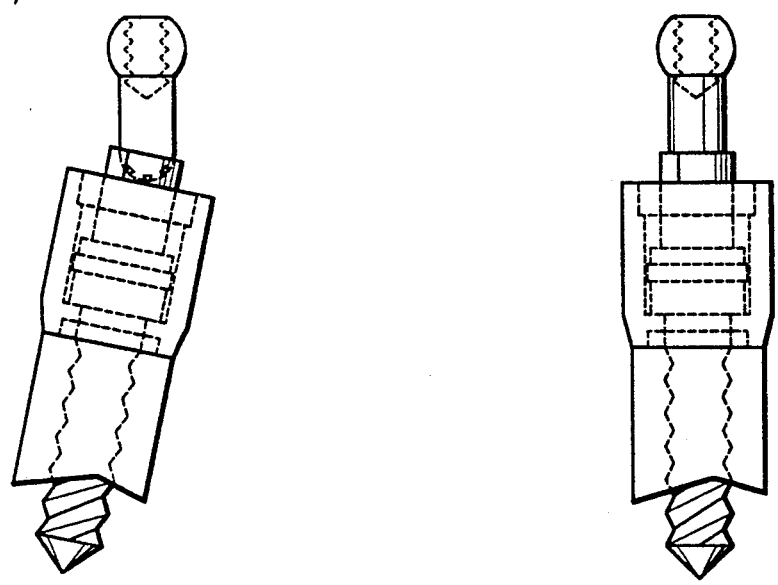
FIG. 10 is an elevational view of the parallel-oriented screw assemblies following the completion of the method.

Referring now to FIG. 8, the jig 30 is then removed by releasing the locks 44 and unscrewing the posts 38 of the adjustment assemblies 34 and 36. The screw portion 11 with the attachment 22 secured thereto (by the resin material) is then removed from the implant fixture 46 and the abutment 47. The resulting assembly is shown in FIG. 9. Thereafter, a soldering pin (not shown) is screwed into the socket 28 of the ball fitting 26 and a soldering analog is secured onto the screw portion. The soldering pin and analog are then placed into a soldering investment and the investment is allowed to dry. With the position of the attachment fixed relative to the screw portion, the resin used to secure the attachment to the screw portion is then burned out. Flux and antiflux material, to facilitate or inhibit solder flow, is then applied to appropriate areas, and these pieces are soldered together. The investment, analog and soldering pin are then removed. Thereafter, the assembly (i.e., the attachment soldered to the screw portion) is finished and polished, and then screwed back into the fixture 46 as seen in FIG. 10.

Thus, even if the implant fixtures are non-parallel, the attachments 22 of the assemblies 10 and 12 are now parallel due to the predetermined positioning of the posts 38 in the intra-oral jig 30. At this point, an overdenture is backed onto the attachments or an impression is taken for indirect fabrication of a prosthesis.

The method can also be effected using a pair of two-piece assemblies, which will be needed when no fixtures are placed in an acceptable restorative position. In such case, the screw portions 11 of each assembly are retained in the implant fixtures and the attachments are screwed onto the threaded shafts 40 of the posts 38. Once the parallel orientation is established, the Duralay resin is applied to both assemblies to secure the attachment to the fitting 16, and the method proceeds as previously described. Of course, the above-described method can also be effected indirectly by taking an impression, creating a working model and using a surveyor.

It should be appreciated by those skilled in the art that the specific embodiments disclosed above may be readily utilized as a basis for modifying or designing other structures for carrying out the same purposes of the present invention. The invention need not be practiced intra-orally, rather the restoration can be fabricated indirectly using traditional impression techniques and applying the method to the model. In such case, the jig is modified as shown in phantom in FIG. 2. In particular, the jig 30 includes a mandrel retention device 45 having a mandrel receptacle 46 therein. This receptacle 46 receives one end of a mandrel 47, the other end of which attaches to a surveyor mechanism. This mandrel attachment facilitates the use of the jig for indirect methods of paralleling implant restorative components according to the invention. Moreover, the teachings of the invention are likewise applicable to paralleling multiple attachments or abutments simultaneously.

Another important application of the method involves paralleling implant components to a representation of a natural tooth on a working model. In this embodiment, one post of the jig is replaced with a paralleling rod of the surveyor mechanism. The working model is first positioned relative to the surveyor such that a desired angulation with respect to the tooth is achieved. The other post of the jig is then secured to a "two-piece" abutment screw assembly, as shown in FIG. 1, and the method proceeds.

It should also be realized by those skilled in the art that such equivalent constructions do not depart from the spirit and scope of the invention as set forth in the appended claims.

What is claimed is:

1. A method for fabricating a dental prosthodontic restoration to be fitted on at least first and second implant fixtures, each of the implant fixtures supporting an abutment, comprising the steps of:
   (a) fitting a first abutment screw assembly to said first implant fixture, the first abutment screw assembly including a screw portion, and an attachment;
   (b) tightening the first abutment screw assembly to retain the first abutment screw assembly in the first implant fixture;
   (c) fitting a screw portion of a second abutment screw assembly to said second implant fixture, the second abutment screw assembly including an attachment that is attachable to the screw portion of the second abutment screw assembly and pivotally adjustable relative thereto;
   (d) tightening the screw portion of the second abutment screw assembly to retain the screw portion in the second implant fixture; and
   (e) using a jig mechanism to precisely locate the attachment of the second abutment screw assembly in a predetermined position relative to the screw portion thereof such that the attachments of the first and second abutment screw assemblies have a parallel orientation.

2. The method as described in claim 1 further including the step of:
(f) securing the attachment of the second abutment screw in the predetermined position using a resin material.

3. The method as described in claim 2 further including the step of:
(g) removing from the second implant fixture the screw portion of the second abutment screw assembly with the attachment secured thereto.

4. The method as described in claim 3 further including the steps of:
(h) burning away the resin material while the attachment is maintained against movement relative to the screw portion;
(i) soldering the attachment to the screw portion; and
(j) polishing and finishing the attachment and the screw portion.

5. The method as described in claim 4 further including the step of:
(k) fitting the second abutment screw assembly to the second implant fixture, whereby the attachments of the first and second abutment screw assemblies are then paralleled.

6. The method as described in claim 5 further including the step of:
(1) placing an overdenture or prosthesis on the paralleled attachments of the first and second abutment screw assemblies.

7. A method for fabricating a dental prosthodontic restoration to be fitted on at least first and second implant fixtures, each of the implant fixtures supporting an abutment, comprising the steps of:
(a) fitting a first abutment screw assembly to said first implant fixture, the first abutment screw assembly including a screw portion, and an attachment secured to the screw portion;
(b) tightening the first abutment screw assembly to retain the first abutment screw assembly in the first implant fixture;
(c) fitting a screw portion of a second abutment screw assembly to said second implant fixture;
(d) tightening the screw portion of the second abutment screw assembly to retain the screw portion in the second implant fixture;
(e) locating an attachment of the second abutment screw assembly in a predetermined position relative to the screw portion thereof such that the attachments of the first and second abutment screw assemblies have a parallel orientation;

(f) securing the attachment of the second abutment screw in the predetermined position using a resin material.

8. The method as described in claim 7 further including the steps of:
(g) removing from the second implant fixture the screw portion of the second abutment screw assembly with the attachment secured thereto;
(h) burning away the resin material while the attachment is maintained against movement relative to the screw portion;
(i) soldering the attachment to the screw portion; and
(j) fitting the second abutment screw assembly to the second implant fixture, whereby the attachments of the first and second abutment screw assemblies are then paralleled.

9. The method as described in claim 8 further including the step of:
(k) placing an overdenture or prosthesis on the paralleled attachments of the first and second abutment screw assemblies.

10. A method for fabricating a dental prosthodontic restoration to be fitted on at least first and second supports, comprising the steps of:
(a) fitting a first assembly to said first support, the first assembly including an attachment;
(b) tightening the first assembly to retain the first assembly in the first support;
(c) fitting a screw portion of an abutment screw assembly to said second support, the abutment screw assembly including an attachment that is attachable to the screw portion of the abutment screw assembly and pivotally adjustable relative thereto;
(d) tightening the screw portion of the abutment screw assembly to retain the screw portion in the second support; and
(e) using a jig mechanism to precisely locate the attachment of the abutment screw assembly in a predetermined position relative to the screw portion thereof such that the attachments of the first assembly and the abutment screw assembly have a parallel orientation.

11. The method as described in claim 10 wherein the first support is a representation of a natural tooth and the second support is an implant fixture.

12. The method as described in claim 10 wherein the first implant fixture is a representation of a natural tooth and the second implant fixture is an implant fixture.

13. The method as described in claim 10 wherein steps (a)–(e) are performed intra-orally.

14. The method as described in claim 10 wherein steps (a)–(e) are performed extra-orally using a working model.

* * * * *